United States Patent [19]

Meier et al.

[11] Patent Number: 5,167,846
[45] Date of Patent: Dec. 1, 1992

[54] SULFOXIDES OF BISTHIOMETHYLATED AND TRISTHIOMETHYLATED PHENOLS

[75] Inventors: Hans-Rudolf Meier, Marly; Rita Pitteloud, Praroman, both of Switzerland

[73] Assignee: Ciba-Geigy Corporation, Ardsley, N.Y.

[21] Appl. No.: 646,588

[22] Filed: Jan. 25, 1991

[30] Foreign Application Priority Data

Feb. 5, 1990 [CH] Switzerland .................. 361/90

[51] Int. Cl.$^5$ .................. C10M 135/08; C07C 323/65
[52] U.S. Cl. ......................... 252/48.2; 252/77; 568/27; 568/36; 524/155
[58] Field of Search ............ 568/27, 36; 252/48.2; 524/155

[56] References Cited

U.S. PATENT DOCUMENTS

| | | | |
|---|---|---|---|
| 3,146,271 | 8/1964 | Louthan | 568/36 |
| 3,227,677 | 1/1966 | Simpson | 524/289 |
| 3,466,377 | 9/1969 | Shunk et al. | 568/27 |
| 3,660,352 | 5/1972 | Song | 252/48.2 |
| 3,772,390 | 11/1973 | Song | 252/48.2 |
| 3,903,173 | 9/1975 | Eggensperger et al. | 568/51 |
| 4,284,790 | 8/1981 | Hinsken et al. | 560/15 |
| 4,741,846 | 5/1988 | Evans | 252/47.5 |
| 4,759,862 | 7/1988 | Meier | 252/47.5 |
| 4,820,756 | 4/1989 | Pitteloud et al. | 524/289 |
| 4,857,572 | 8/1989 | Meier et al. | 252/48.1 |
| 4,874,885 | 10/1989 | Stegmann et al. | 560/15 |

FOREIGN PATENT DOCUMENTS

| | | |
|---|---|---|
| 273013 | 12/1987 | European Pat. Off. . |
| 441742 | 8/1991 | European Pat. Off. .......... 568/36 |
| 7427092 | 7/1965 | Japan . |
| 6803773 | of 1968 | Japan . |
| 6816741 | of 1968 | Japan . |
| 6809052 | of 1974 | Japan . |
| 917370 | 2/1963 | United Kingdom . |
| 1396469 | 6/1975 | United Kingdom . |

OTHER PUBLICATIONS

CA 115(23):255805b.
Derwent Abstr. 09,8630Q (1964).
Chem. Abstr. 70:77582U (1969).
Derwent Abstr. 00,893Q (1964).
Angew, Makromol. Chem. vol. 82 pp. 197-205 (1979).
Derwent Abstract JA 040726 (1974).
Chem. Abstract 69:96239h (1968).

Primary Examiner—Ellen McAvoy
Attorney, Agent, or Firm—JoAnn Villamizar

[57] ABSTRACT

Sulfoxides of bisthiomethylated and tristhiomethylated phenols of formulae I and II

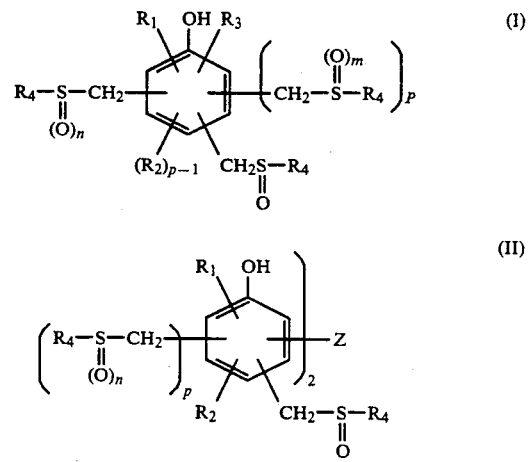

wherein
$R_1$ is hydrogen, $C_1$-$C_{18}$alkyl, cyclohexyl or $C_7$-$C_9$-phenylalkyl,
$R_2$ and $R_3$ are each independently of the other hydrogen or methyl,
$R_4$ is $C_4$-$C_{18}$alkyl, phenyl, $C_7$-$C_9$phenylalkyl, $C_1$-$C_4$alkyl-substituted phenyl, hydroxyethyl or a radical $-(CH_2)_r COOR_5$, wherein r is 1 or 2 and $R_5$ is $C_1$-$C_{18}$alkyl,
Z is sulfur

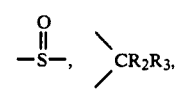

wherein $R_2$ and $R_3$ are as defined above, or are a direct bond, and n, m and p are each independently of one another 0 or 1, and mixtures thereof with the corresponding non-oxidized compounds, are suitable stabilizers for materials which are sensitive to oxidative, thermal and/or light-induced degradation.

23 Claims, No Drawings

SULFOXIDES OF BISTHIOMETHYLATED AND TRISTHIOMETHYLATED PHENOLS

The present invention relates to sulfoxides of bisthiomethylated and tristhiomethylated phenols, to mixtures of said sulfoxides with the non-oxidised compounds, to compositions of organic polymers containing these compounds or mixtures, and to the use of said compounds and mixtures as stabilisers for materials which are sensitive to oxidative, thermal or light-induced degradation.

Thiomethylated phenols are used as stabilisers in organic polymers. The use of 2,4,6-trisubstituted bis(3,5-alkylthiomethyl)phenols as antioxidants in elastomers is disclosed in U.S. Pat. Nos. 3,660,352 and 4,820,756. The use of 2,6-bis(alkoxycarbonylalkylthiomethyl)-4-alkylphenols as antioxidants for polyolefins is disclosed in U.S. Pat. No. 3,227,677. o,p-Alkylthiomethylphenols are disclosed in U.S. Pat. No. 4,857,572 and 4,759,862. Further alkylthiomethylphenols are disclosed in U.S. Pat. No. 4,874,885 and in EP-A-273 013. 2,4,6-Tris(alkylthiomethyl)phenols are disclosed in U.S. Pat. No. 4,741,846. Compounds such as 4,4'-thiobis(2-methyl-tert-butylphenol) and the corresponding compounds which are mono- or dioxidised at the sulfur atom have been investigated as antioxidants by Jiráčková and Pospíšil in Angewandte Makromolekulare Chemie 82 (1979), 197–205.

Oxidation products of o-tert-butyl-substituted alkylthiomethylated phenols are disclosed in JP-A-68-09 052, JP-A-68-16 741, JP-A-68-03 773 and JP-A-74-27 092. Bis(dihydrocarbylhydroxybenzyl)sulfides are disclosed in GB-A-917 370.

In the field of antioxidants for organic polymers there still exists a need for useful compounds. Especially in the field of elastomers and lubricants, novel utilities and novel compositions make adaptations necessary with respect to stabilising these substrates. It has now been found that specific sulfoxides of bisthiomethylated and tristhiomethylated phenols are very suitable for stabilising materials which are sensitive to oxidative, thermal and light-induced degradation.

Specifically, the invention relates to compounds of formulae I and II

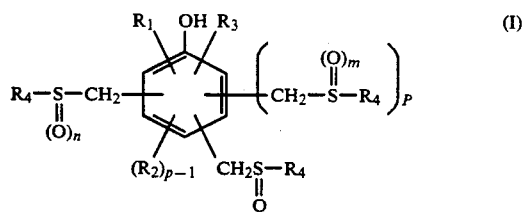 (I)

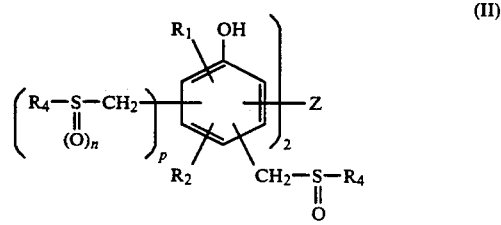 (II)

wherein
$R_1$ is hydrogen, $C_1$–$C_{18}$alkyl, cyclohexyl or $C_7$–$C_9$phenylalkyl,
$R_2$ and $R_3$ are each independently of the other hydrogen or methyl,
$R_4$ is $C_4$–$C_{18}$alkyl, phenyl, $C_7$–$C_9$phenylalkyl, $C_1$–$C_4$alkyl-substituted phenyl,
hydroxyethyl or a radical —$(CH_2)_r$COOR$_5$, wherein r is 1 or 2 and $R_5$ is $C_1$–$C_{18}$alkyl
Z is sulfur,

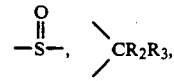 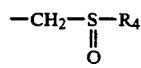

wherein $R_2$ and $R_3$ are as defined above, or is a direct bond, and n, m and p are each independently of one another 0 or 1.

$R_1$ and $R_5$ as $C_1$–$C_{18}$alkyl may be linear or branched and are typically methyl, ethyl, n-propyl, isopropyl, n-butyl, tert-butyl, n-pentyl, isopentyl, n-hexyl, 2-ethylhexyl, n-heptyl, n-octyl, isooctyl, decyl, dodecyl, tetradecyl or octadecyl.

Preferably $R_1$ is hydrogen or $C_1$–$C_{12}$alkyl such as $C_1$–$C_4$alkyl, more particularly methyl, ethyl, isopropyl or tert-butyl and, most preferably, methyl or tert-butyl.

$R_5$ is preferably $C_6$–$C_{12}$alkyl such a $C_8$–$C_{12}$alkyl, most preferably octyl, typically 2-ethylhexyl.

$R_1$ as $C_7$–$C_9$phenylalkyl is typically benzyl, phenylethyl, α-methylbenzyl, 3-phenylpropyl, 2-methylphenylethyl, 1-methylphenylethyl or α,α-dimethylbenzyl. Benzyl is preferred.

$R_4$ as $C_4$–$C_{18}$alkyl may be linear or branched and is typically n-butyl, tert-butyl, n-pentyl, isopentyl, n-hexyl, n-heptyl, n-octyl, isooctyl, 2-ethylhexyl, 1,1,3,3-tetramethylbutyl, n-nonyl, n-decyl, n-dodecyl, 1,1,3,3,5,5-hexamethylhexyl or 1,1,4,6,6-pentamethylhept-4-yl.

$R_4$ is preferably $C_6$–$C_{18}$alkyl, most preferably $C_8$–$C_{12}$alkyl, and is typically n-octyl, 1,1,3,3-tetramethylbutyl or n-dodecyl.

$R_4$ as $C_7$–$C_9$phenylalkyl may have the same meanings as indicated previously for $R_1$.

$R_4$ as $C_1$–$C_4$alkyl-substituted phenyl may contain 1 to 3, preferably 1 or 2 alkyl groups, preferably methyl groups. Exemplary of such groups are tolyl, xylyl and mesityl. Preferably $R_4$ is $C_4$–$C_{18}$alkyl, phenyl, $C_7$–$C_9$phenylalkyl or —CH$_2$COOR$_5$, wherein $R_5$ is $C_6$–$C_{12}$alkyl.

Z is preferably methylene or sulfur. The substituent

—CH$_2$—S—R$_4$
    ‖
    O in formula II is preferably in m- or p-position to Z, in which case p is preferably 0.

Particularly interesting compounds of formulae I and II are those wherein p is O, $R_4$ is $C_4$–$C_{18}$alkyl, phenyl, $C_7$–$C_9$phenylalkl, hydroxyethyl or a radical —CH$_2$COOR$_5$, wherein $R_5$ is $C_1$–$C_{18}$alkyl and $R_1$, $R_2$, $R_3$, Z, n and m are as defined above.

Compounds of formula I are especially prefered wherein p is 0, $R_1$ is hydrogen, $C_1$–$C_4$-alkyl or cyclohexyl, $R_4$ is $C_4$–$C_{18}$alkyl, preferably $C_8$–$C_{12}$alkyl, benzyl, phenyl, hydroxyethyl or —CH$_2$COOR$_5$, $R_5$ is $C_1$–$C_{18}$alkyl, and $R_2$, $R_3$, Z, m, n and p are as previously defined.

Particularly interesting compounds of formula I are those wherein p is 0 and the groups

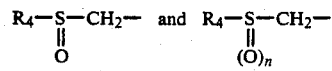

are in 2,4- or 2,6- or 3,5-position to the OH group, and $R_1$, $R_2$, $R_3$, $R_4$, $R_5$, Z, n and m are as defined above.

Particularly preferred compounds of formula I are those wherein $R_1$ is hydrogen or $C_1$-$C_4$-alkyl, $R_4$ is $C_8$-$C_{12}$alkyl, hydroxyethyl or a radical —$CH_2COOR_5$, wherein $R_5$ is $C_8$-$C_{12}$alkyl, and $R_2$, $R_3$, Z, m, n and p are as defined above and the groups

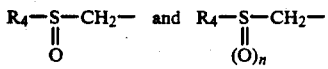

are in 2,4- or 2,6-or 3,5-position to the OH group.

Compounds of very particular interest are those of formula III

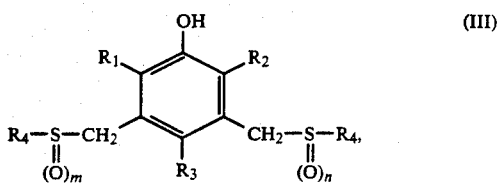

wherein $R_1$ is hydrogen, $C_1$-$C_4$alkyl or cyclohexyl, $R_2$, $R_3$, n and m are as defined for formula I, with the proviso that $n+m$ is$\geq 1$, and $R_4$ is $C_4$-$C_{18}$alkyl, phenyl, $C_7$-$C_9$phenylalkyl, hydroxyethyl or a radical —$CH_2COOR_5$, wherein $R_5$ is $C_1$-$C_{18}$alkyl.

Also especially preferred are compounds of formula IV

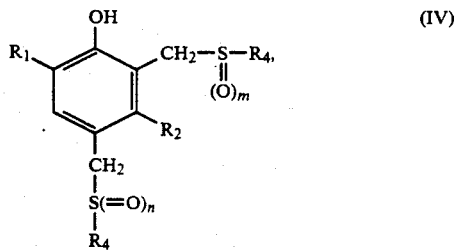

wherein $R_1$ is $C_1$-$C_4$alkyl, $R_2$, n and m are as defined for formula I, with the proviso that $n+m$ is$\geq 1$, and $R_4$ has the same meaning as in formula III.

Further particularly preferred compounds are those of formula V

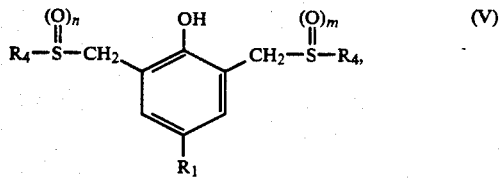

wherein $R_1$ is $C_1$-$C_{12}$alkyl, and n and m are as defined for formula I, with the proviso that $n+m$ is$\geq 1$, and $R_4$ has the same meaning as in formula III.

The invention also relates to mixtures of at least one compound of formula I and/or II with at least one compound of formula VI and/or VII

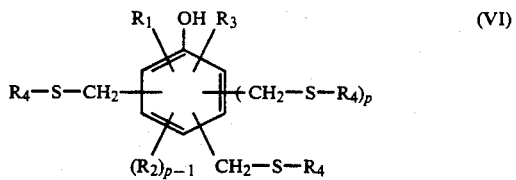

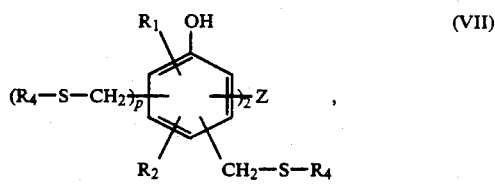

wherein $R_1$, $R_2$, $R_3$, $R_4$, Z and p are as defined for formulae I and II. Preferred meanings are those also given hereinabove in respect of substituents having the same name.

Preferred mixtures are those in which the components of formulae I and II differ from those of formulae VI and VII only in the feature that the latter contain —S— groups in place of the

groupings but otherwise have the same structure as the former.

Further preferred mixtures are those which are obtained by partial oxidation of at least one compound of formula VI and/or VII.

The ratio of the mixtures of at least one compound of formula I and/or II with at least one compound of formula VI and/or VII is 0.5:99.5 to 99.5:0.5. Preferred mixture ratios are from 90:10 to 10:90, most preferably from 80:20 to 20:80.

The compounds of formulae I and/or II and the mixtures thereof with compounds of formula VI and VII, are highly suitable for stabilising organic materials which are sensitive to oxidative, thermal and/or light-induced degradation.

Accordingly, the invention further relates to compositions which comprise an organic material which is sensitive to oxidative, thermal and/or light-induced degradation and at least one compound of formula I and/or II or a mixture of at least one compound of formula I and/or II with at least one compound of formulae VI and/or VII, and to the use of said compounds and mixtures for stabilising organic materials which are sensitive to oxidative, thermal and/or light-induced degradation. Exemplary of such organic materials present in the compositions of this invention and which can be stabilised in the practice of this invention are the following materials:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which can be uncrosslinked or crosslinked), for example high density polyethylene (HDPE), low density polyethylene (LDPE and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers linear low density polyethylene (LLDPE) and mixtures thereof with low density polyethylene (LDPE), propylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate or ethylene/acrylic acid copolymers and their salts (ionomers), as well as terpolymers of ethylene with propylene and a diene such as hexadiene, dicyclopentadiene or ethylidenenorbornene; and also mixtures of such copolymers with each other and with polymers mentioned in 1) above, for example polypropylene/ethylene propylene copolymers, LDPE/ethylene-vinyl acetate copolymers, LDPE/ethylene-acrylic acid copolymers, LLDPE/ethylene-vinyl acetate copolymers and LLDPE/ethylene-acrylic acid copolymers.

3a. Hydrocarbon resins (for example $C_5$–$C_9$), including hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, for example styrene[ch-]butadiene, styrene/acrylonitrile, styrene/alkylmethacrylate, styrene/butadiene/alkylacrylate, styrene/maleic anhydride, styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or α-methylstyrene, for example styrene on polybutadiene, styrene on polybutadiene/styrene or polybutadiene/acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyalkylacrylates or polyalkylmethacrylates, styrene and acrylonitrile on acrylate/butadiene copolymers, as well as mixtures thereof with the copolymers listed under 5), for example the copolymer mixtures known as ABS, MBS, ASA or AES polymers.

7. Halogenated polymers such as polychloroprene, chlorinated rubbers, chlorinated or sulfochlorinated polyethylene, copolymers of ethylene and chlorinated ethylene, epichlorohydrin homo- and copolymers, preferably polymers of halogenated vinyl compounds, for example poly-vinylchloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from α,β-unsaturated acids and derivatives thereof, such as polyacrylates and polymethacrylates, polyacrylamides and polyacrylonitriles.

9. Copolymers of the monomers mentioned under 8) with each other or with other unsaturated monomers, for example acrylonitrile/butadiene copolymers, acrylonitrile/alkylacrylate copolymers, acrylonitrile/alkoxyalkylacrylate or acrylonitrile/vinyl halide copolymers or acrylonitrile/alkylmethacrylate/butadiene terpolymers.

10. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinylbutyrate, polyallyl phthalate or polyallylmelamine; as well as their copolymers with the olefins mentioned in 1) above.

11. Homopolymers and copolymers of cyclic ethers such as polyalkylene glycols, polyethylene oxide, polypropylene oxide or copolymers thereof with bisglycidyl ethers.

12. Polyacetals such as polyoxymethylene and those polyoxymethylenes which contain ethylene oxide as a comonomer; polyacetals modified with thermoplastic polyurethanes, acrylates or MBS.

13. Polyphenylene oxides and sulfides and mixtures thereof with polystyrene or polyamides.

14. Polyurethanes which are derived from polyethers, polyesters or polybutadienes carrying terminal hydroxyl groups on the one hand and aliphatic or aromatic polyisocyanates on the other, as well as precursors thereof.

15. Polyamides and copolyamides which are derived from diamines and dicarboxylic acids and [ch] or from aminocarboxylic acid or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylenediamine and isophthalic and/or terephthalic acid, with or without an elastomer as modifier, for example poly-2,4,4,-trimethylhexamethylene terephthalamide or poly-m-phenylene isophthalamide; block copolymers of the aforementioned polyamides with polyolefins, olefin copolymers, ionomers or chemically bonded or grafted elastomers; or with polyethers, for example with polyethylene glycol, polypropylene glycol or polytetramethylene glycol; and also polyamides or copolyamides modified with EPDM or ABS, and polyamides condensed during processing (RIM polyamide systems).

16. Polyureas, polyimides and polyamide-imides and polybenzimidazoles.

17. Polyesters derived from dicarboxylic acids and diols and/or from hydroxycarboxylic acids or the corresponding lactones, such as poly-ethylene terephthalate, polybutylene terephthalate, poly-1,4-dimethylolcyclohexane terephthalate, polyhydroxybenzoates as well as block-copolyether esters derived from hydroxyl-terminated polyethers; and also polyesters modified with polycarbonates or MBS.

18. Polycarbonates and polyester carbonates.

19. Polysulfones, polyether sulfones and polyether ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Crosslinkable acrylic resins derived from substituted acrylic esters such as epoxy acrylates, urethane acrylates or polyester acrylates.

24. Alkyd resins, polyester resins or acrylate resins which are cross-linked with melamine resins, urea resins, polyisocyanates or epoxy resins.

25. Crosslinked epoxy resins which are derived from polyepoxides, for example from bisglycidyl ethers or from cycloaliphatic diepoxides.

26. Natural polymers such as cellulose, rubber, gelatine and chemically modified homologous derivatives thereof such as cellulose acetates, cellulose propionates and cellulose butyrates, or the cellulose ethers, such as methylcellulose; as well as rosins and their derivatives.

27. Mixtures (polyblends) of the aforementioned polymers, for example PP/EPDM, Polyamide 6/EPDM or ABS, PVC/EVA, PVS/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPO.

28. Naturally occurring and synthetic organic materials which are pure monomeric compounds or mixtures of such compounds, for example mineral oils, animal and vegetable fasts, oil and waxes, or oils, fats and waxes based on synthetic esters (e.g. phthalates, adipates, phosphates or trimellitates) and also the mixtures of synthetic esters with mineral oils in any weight ratios which are used as spinning compositions, as well as aqueous emulsions of such materials.

29. Aqueous emulsions of natural or synthetic rubber, for example natural latex or latices of carboxylated styrene/butadiene copolymers.

The compositions conveniently contain 0.01 to 10% by weight, more particularly 0.05 to 5.0% by weight, preferably 0.05 to 3% by weight, for example 0.1 to 2% by weight, of the compounds or mixtures of the invention, based on the organic material.

The material which is sensitive to oxidative, thermal and/or light-induced degradation may be, for example, an organic polymer, lubricant or a hydraulic fluid. Organic polymers are preferably synthetic polymers, especially elastomers.

Especially preferred compositions contain elastomers or lubricants and at least one compound of formula I or a mixture of at least one compound of formula I with at least one compound of formula VI.

The suitable lubricants are based, for example, on mineral or synthetic oils or mixtures thereof. The lubricants are known to the skilled person and are described in the relevant literature, as for example in Dieter Klamann, "Schmierstoffe und verwandte Produkte" (Verlag Chemie, Weinheim, 1982), in Schewe-Kobek, "Das Schmiermittel-Taschenbuch" (Dr. Alfred Hüthig-Verlag, Heidelberg, 1974) and in "Ullmanns Enzyklopädie der technischen Chemie", Vol. 13, pages 85-94 (Verlag Chemie, Weinheim, 1977).

The lubricants are preferably oils and fats, for example based on a mineral oil. Oils are preferred.

A further group of eligible lubricants are vegetable or animal oils, fats, tallows and waxes or mixtures thereof with one another or mixtures withe the cited mineral or synthetic oils. Exemplary of vegetable or animal oils, fats, tallows and waxes are palm nut oil, palm oil, olive oil, rape oil, grund nut oil, soybean oil, cottonseed oil, sunflower oil, pumpkin seed oil, coconut oil, corn oil, castor oil, and mixtures thereof, fish oils, tallows from slaughter animals such as beef tallow, neat's foot oil and bone oil, and the modified, epoxidised and sulfoxidised forms thereof, for example epoxidised soybean oil.

The mineral oils are based in particular on hydrocarbon compounds.

Synthetic lubricants typically comprise lubricants based on aliphatic or aromatic carboxylates, polymeric esters, polyalkylene oxides, phosphates, poly-α-olefins or silicones, a diester of a divalent acid with a monohydric alcohol, for example dioctyl sebacate or dinonyl adipate, a triester of trimethylolpropane with a monovalent acid or with a mixture of such acids, for example trimethylolpropane triple argonate, trimethylolpropane tricaprylate or mixtures hereof, a tetraester of pentaerythritol with a monovalent acid or with a mixture of such acids, for example pentaerythritol tetracaprylate, or on a complex ester of trimethylolpropane with caprylic and sebacic acid, or on a mixture thereof. Aside from mineral oils, particularly suitable are, for example, poly-α-olefins, lubricants based on esters, phosphates, glycols, polyglcols, as well as mixtures thereof with water.

The compositions of this invention may contain the following materials as suitable elastomers:

1. Polydienes such as polybutadiene, polyisoprene or polychloroprene; block polymers such as styrene/butadiene/styrene, styrene/isoprene/styrene or acrylonitrile/butadiene copolymers.

2. Copolymers of momoolefins and diolefins with each other or with other vinyl monomers, for example ethylene/alkyl acrylates, ethylene/alkyl methacrylates, ethylene/vinyl acetate or ethylene/acrylic acid copolymers and terpolymers of ethylene with propylene and a diene such as hexadiene, dicyclopentadiene or ethylidenenorbornene.

3. Halogen-containing polymers, e.g. polychloroprene, chlorinated rubber, chlorinated or sulfochlorinated polyethylene, epichlorohydrin homo- and copolymers, chlorotrifluoroethylene copolymers, polymers from halogen-containing vinyl compounds, e.g. polyvinylidene chloride, polyvinylidene fluoride, as well as copolymers thereof, for example vinyl chloride/vinylidene chloride, vinyl chloride/vinyl acetate or vinylidene chloride/vinyl acetate copolymers.

4. Polyurethanes which are derived from hydroxyl-terminated polyethers, polyesters and polybutadiene on the one hand and from aliphatic or aromatic polyisocyanates on the other, as well as precursors thereof.

5. Natural rubber.

6. Mixtures (polyblends) of the above-mentioned polymers.

7. Aqueous emulsions of natural or synthetic rubbers, e.g. natural latex or latices of carboxylated styrene/butadiene copolymers.

These elastomers may be in the form of latices and can be stabilised as such.

Preferred compositions are those wherein the elastomer is a polydiene such as polybutadiene rubber, a halogenated polymer such as polyvinylidene fluoride, or a polyurethane.

Incorporation of the compounds or mixtures of this invention and further optional additives into the organic materials is effected by methods commonly employed in the art. If the organic materials are polymers, especially synthetic polymers, incorporation can be effected before or during shaping to moulded articles or by applying the dissolved or dispersed compounds to the polymer, with or without subsequent evaporation of the solvent. In the case of elastomers, these may also be stabilised as latices. A further means of incorporating the compounds or mixtures of this invention consists in adding them before or during the polymerisation to the appropriate monomer or before crosslinking. If addition is made before or during the polymerisation, the compounds of formula I or II, or the mixtures of compounds of formulae I and/or II with at least one compound of formula VI and/or VII, may also act as regulators for the chain length of the polymerisation (chain terminators).

The compounds of the invention or mixtures thereof may also be added in the form of a masterbatch which contains these compounds in a concentration of, for example, 2.5 to 25% by weight, to the plastics materials to be stabilised.

Polymer compositions of this invention may be used in a variety of forms and processed to different products, for example to sheets, filaments, ribbons, mouldings, profiles, or used as binders for paints and varnishes, adhesives or putties.

Lubricant compositions of the invention may be used in internal combustion engines, for example in motor vehicles.

In addition to the compounds or mixtures of this invention, the compositions—especially if they contain organic, preferably synthetic, polymers—may contain further conventional additives. Illustrative examples of such additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl)isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6. Acylaminophenols, for example 4-hydroxylauranilide, 4-hydroxystearanilide, 2,4-bis(octylmercapto)-6-(3,5-di-tert-butyl-4-hydroxyanilino)-s-triazine, octyl N-(3,5-di-tert-butyl-4-hydroxyphenyl)carbamate.

1.7. Esters of $\beta$-(3,5-di-tert-butyl-4-hydroxyphenyl)propionic acid with mono- or polyhydric alcohols, e.g. with methanol, octadecanol, 1,6-hexanediol, neopentyl glycol, triethylene glycol, pentaerythritol, tris(hydroxyethyl) isocyanurate, thiodiethylene glycol, N,N'-bis(hydroxyethyl)oxalodiamide.

1.8. Esters of $\beta$-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalodiamide.

1.9. Esters of $\beta$-(3,5-dicyclohexyl-4-hydroxyphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalodiamide.

1.10. Amides of $\beta$-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis($\alpha,\alpha$-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)-resorcinol, benzoylresorcinol, 2,4-di-tert-butylphenyl 3,5-di-tert-butyl-4-hydroxy-benzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzyl-phosphonic acid monoalkyl esters, e.g. of the methyl or ethyl ester, nickel complexes of ketoximes, e.g. of 2-hydroxy-4-methyl-phenyl undecyl ketoneoxime, nickel complexes of 1-phenyl-4-lauroyl-5-hydroxypyrazole, with or without additional ligands.

2.6. Sterically hindered amines, for example bis(2,2,6,6-tetramethyl-piperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxy-benzylmalonate, the condensation product of 1-(2-hydroxyethyl)-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)bis-(3,3,5,5-tetramethylpiperazinone).

2.7. Oxalyl diamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butoxanilide and mixtures of ortho- and para-methoxy-disubstituted oxanilides and mixtures of o- and p-ethoxydisubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxy-phenyl)-4,6-bis(2,4-dimethylphenyl)-1,3,5-triazine, 2-(2,4-dihydroxy-phenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalyl diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloyl-amino-1,2,4-triazole, bis(benzylidene)oxalic dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-ditertbutylphenyl) pentaerythritol diphosphite, tristearyl sorbitol triphosphite, tetrakis-(2,4-di-tert-butylphenyl) 4,4'-biphenylene diphosphonite, 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in conjunction with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, fluorescent whitening agents, flameproofing agents, antistatic agents and blowing agents.

If the compositions of the invention are lubricant compositions and hydraulic fluids, they may contain further additives. These further additives are added to improve certain performance properties and are, typically, further antioxidants, metal deactivators, rust inhibitors, viscosity index improvers, pour-point depressants, dispersants/surfactants and antiwear additives. Illustrative examples of antioxidants are those listed above under item "1. Antioxidants", especially under items 1.1 to 1.10. 11 Further suitable antioxidants are typically:

Examples of amine antioxidants:

N,N'-diisopropyl-p-phenylenediamine, N,N'-di-sec-butyl-p-phenylenediamine, N,N'-bis-(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(naphthyl-2)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, mixture of mono- and dialkylated tert-butyl/tert-octyldiphenylamines, 2,3-dihydro-3,3-dimethyl-4H-1,4-benzothiazine, phenothiazine, N-allylphenothiazine.

Examples of further antioxidants:

Aliphatic or aromatic phosphites, esters of thiodipropionic acid or of thiodiacetic acid, or salts of dithiocarbamic or dithiophosphoric acid.

Examples of metal deactivators, for example for copper, are:

triazoles, benzotriazoles and derivatives thereof, tolutriazoles and derivatives thereof, 2-mercaptobenzothiazole, 2-mercaptobenzotriazole, 2,5-dimercaptobenzotriazole, 2,5-dimercaptobenzothiadiazole, 5,5'-methylenebisbenzotriazole, 4,5,6,7-tetrahydrobenzotriazole, salicylidene propylenediamine, salicylaminoguanidine and the salts thereof.

Examples of rust inhibitors are:

a) organic acids and the esters, metal salts and anhydrides thereof, for example:
  N-oleoyl sarcosine, sorbitan monooleate, lead naphthenate, alkenylsuccinic anhydride, for example dodecenylsuccinic anhydride, alkenylsuccinic partial esters and partial amides, 4-nonylphenoxyacetic acid.

b) Nitrogen-containing compounds, for example:
  I. Primary, secondary or tertiary aliphatic or cycloaliphatic amines and amine salts of organic and inorganic acids, for example oil-soluble alkylammonium carboxylates.
  II. Heterocyclic compounds, for example: substituted imidazolines and oxazolines.

c) Phosphorus-containing compounds, for example:
  amine salts of phosphoric acid partial esters or phosphonic acid partial esters, zinc dialkyldithiophosphates.

d) Sulfur-containing compounds, for example:
  barium dinonylnaphthalene sulfonates, calcium petroleum sulfonates.

Examples of viscosity index improvers are:

polyacrylates, polymethacrylates, vinyl pyrrolidone/methacrylate copolymers, polyvinylpyrrolidones, polybutenes, olefin copolymers, styrene/acrylate copolymers, polyethers.

Examples of pour-point depressants are:

polymethacrylates, alkylated naphthalene derivatives.

Examples of dispersants/surfactants are:

polybutenylsuccinamides or -imides, polybutenylphosphonic acid derivatives, basic magnesium, calcium, and barium sulfonates and phenolates.

Examples of antiwear additives are:

sulfur and/or phosphorus and/or halogen-containing compounds such as sulfonated vegetable oils, zinc dialkyl dithiophosphates, tritolylphosphate, chlorinated paraffins, alkyl and aryldi- and trisulfides, triphenylphosphorothionates, diethanolaminomethyltolyltriazole, bis(2-ethylhexyl)aminomethyltolyltriazole.

The sulfoxides of formulae I and II can be obtained, for example, by oxidising compounds of formula VI or VII. Suitable oxidising agents are typically hydrogen peroxide or percarboxylic acids, organic hydroperoxides or other suitable organic or inorganic oxidising agents. The methods known in the relevant literature may be used. Exemplary of suitable percarboxylic acids are m-chloroperbenzoic acid, peracetic acid or trifluoroperacetic acid. Tert-butylhydroperoxide or cumene peroxide may be used as hydroperoxides.

The oxidation of the starting materials can also be carried out with oxidising agents which are formed in situ. Such oxidising agents are, typically, percarboxylic acids which form in a mixture of hydrogen peroxide and carboxylic acids.

Depending on the desired product, the oxidising agent is conveniently added in stoichiometric amount or in excess. The reaction parameters are chosen such that the sulfoxides are oxidised to the sulfones to as minor a degree as possible. The oxidation is conveniently carried out in the presence of a solvent. Illustrative examples of suitable solvents are non-oxidisable organic solvents such as chlorinated hydrocarbons, ketones or hydrocarbons. Exemplary of chlorinated hydrocarbons are methylene chloride or chloroform. Suitable ketones are acetone, methyl ethyl ketone or methyl isopropyl ketone. Particularly suitable hydrocarbons are aromatic hydrocarbons such as toluene or xylene.

The reaction temperature can be in the range from $-40°$ to $+80°$ C. Depending on the temperature and specific reaction, the reaction times are typically from 10 minutes to 24 hours.

The starting materials, the compounds of formulae VI and VII and their preparation are known from the literature and disclosed in numerous patents, for example in U.S. Pat. Nos. 4,759,862; 4,857,572; 3,772,390; 4,874,885 and 4,820,756 or in FR-A 156 9743.

The oxidation of compounds of formulae VI and VII normally gives mixtures of compounds of formulae I and II (products oxidised at one and/or more —CH$_2$—S—R$_4$— groups; q.v. Example 1). These mixtures can be used direct in the compositions of the invention. They can also, however, be resolved into the individual components by conventional methods such as chromatography, fractional crystallisation and the like.

The preparation of the mixtures of compounds of formulae I and II and those of formulae VI and VII can be effected, for example, by mixing the individual compounds in the desired ratio. Preferably, however, these mixtures are obtained by partial oxidation of compounds of formulae VI and VII by the above methods, using the oxidising agent in less than stoichiometric amount. The amount of oxidising agent will depend on the desired content of compound of formula I and/or II in the mixture and can be readily ascertained by simple experimentation or computation. Further details will be found in the Examples.

The invention is illustrated by the following Examples in which, and also throughout the remainder of the specification and the claims, parts and percentages are by weight, unless otherwise stated.

EXAMPLE 1

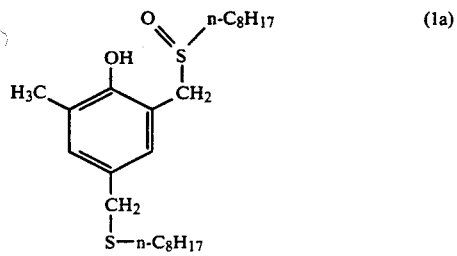

(Ia)

-continued

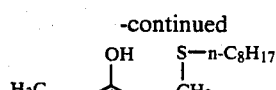
(1b)

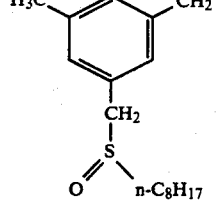
(1c)

127.42 g of 2,4-bis(n-octylthiomethyl)-6-methylphenol are dissolved in 750 ml of acetone, and 17 g of 30% hydrogen peroxide are added dropwise to this solution at 0°–5° C. over 10 minutes. After stirring for 2½ hours at 0° C., the solvent is removed by distillation under reduced pressure. The residue is chromatographed over silica gel with hexane/ethyl acetate (7:3) as eluant, to give 33.7 g of 2-methyl-6-n-octylsulfinylmethyl-4-n-octylthiomethylphenol (1a) as an oil, 6.2 g of 2-methyl-4-n-octylsulfinylmethyl-6-n-octylthiomethylphenol (1b), melting point: 105°–106° C., and 16.9 g of 2,4-bis(n-octylsulfinylmethyl)-6-methylphenol (1c), melting point: 92° C.

|  |  | Elemental analysis in % | |
|---|---|---|---|
|  |  | calculated | found |
| Example 1a | C | 68.13 | 68.27 |
|  | H | 10.06 | 9.92 |
|  | S | 14.55 | 14.26 |
| Example 1b | C | 68.13 | 68.28 |
|  | H | 10.06 | 10.21 |
|  | S | 14.55 | 14.54 |
| Example 1c | C | 65.74 | 65.85 |
|  | H | 9.71 | 9.70 |
|  | S | 14.04 | 14.01 |

EXAMPLES 2–18

The compounds of Examples 2–18 are prepared in accordance with the following procedure:

0.1 mol of the respective bisalkylthiomethylphenol of formula VI is dissolved in methylene chloride, and 0.11 mol of 30% hydrogen peroxide is added dropwise at 0°–20° C. over 5–10 minutes to this solution to obtain the monooxidised compound and 0.22 mol of 30% hydrogen peroxide to obtain the dioxidised compound. The solution is stirred for 2 hours at 0° C. The products are obtained pure by column chromatography over silica gel. The resultant products are listed in Table 1.

TABLE 1

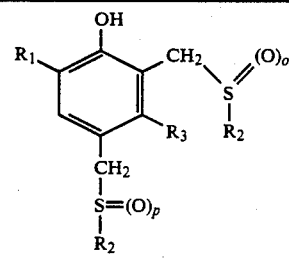

| Ex. | $R_1$ | $R_2$ | $R_3$ | o | p | m.p. [°C.] | Ratio of compound of formula VI/$H_2O_2$ | Eluant |
|---|---|---|---|---|---|---|---|---|
| 2 | t-butyl | n-$C_8H_{17}$ | H | 1 | 0 | oil | 1:1 | D |
| 3 | t-butyl | n-$C_8H_{17}$ | H | 0 | 1 | oil | 1:1 | D |
| 4 | t-butyl | n-$C_8H_{17}$ | H | 1 | 1 | oil | 1:2 | D |
| 5 | methyl | n-$C_{12}H_{25}$ | H | 1 | 0 | 47 | 1:1 | A |
| 6 | methyl | n-$C_{12}H_{25}$ | H | 0 | 1 | 106 | 1:1 | A |
| 7 | methyl | n-$C_{12}H_{25}$ | H | 1 | 1 | 97 | 1:1 | A |
| 8 | methyl | $CH_2CH_2OH$ | H | 1 | 0 | oil | 1:1 | B |
| 9 | methyl | $CH_2CH_2OH$ | H | 0 | 1 | oil | 1:1 | B |
| 10 | methyl | $CH_2CH_2OH$ | H | 1 | 1 | 120 | 1:1 | B |
| 11 | methyl | $CH_2COO$-2-EH* | H | 1 | 0 | oil | 1:2 | A |
| 12 | methyl | $CH_2COO$-2-EH* | H | 0 | 1 | oil | 1:2 | A |
| 13 | methyl | $CH_2COO$-2-EH* | H | 1 | 1 | oil | 1:2 | A |
| 14 | methyl | n-$C_{12}H_{25}$ | methyl | 1 | 0 | 74 | 1:1 | A |
| 15 | methyl | n-$C_{12}H_{25}$ | methyl | 0 | 1 | 84 | 1:1 | A |
| 16 | t-butyl | n-$C_{12}H_{25}$ | methyl | 1 | 1 | 122 | 1:1 | A |
| 17 | t-butyl | n-$C_{12}H_{25}$ | methyl | 1 | 0 | 55 | 1:1 | C |
| 18 | t-butyl | n-$C_{12}H_{25}$ | methyl | 1 | 1 | 97 | 1:1 | C |

*2-EH = 2-ethylhexyl
A = hexane/ethyl acetate (7:3)
B = hexane/acetone (1:2)
C = hexane/ethyl acetate (9:1)
D = hexane/ethyl acetate (4:1)

Characteristic $^1$H-NMR signals of compounds of Examples 1–18, measured in deuterochloroform at 100 MHz (standard: tetramethylsilane) are given in Table 2.

TABLE 2

| Ex. | Aryl—C$\underline{H_2}$—S=O δ [ppm] | $J_{AB}$ [Hz] | Aryl—C$\underline{H_2}$SR δ [ppm] | Aryl—C$\underline{H_2}$S(=O)CH$_2$ δ [ppm] | Aryl—CH$_2$—S—C$\underline{H_2}$ δ [ppm] | J [Hz] |
|---|---|---|---|---|---|---|
| 1a | 4.38/3.78 | 14 | 3.60 | | 2.25–2.79 (m) | |
| 1b | 3.93/3.76 | 14 | 3.77 | | 2.32–2.66 (m) | |
| 1c | 4.36/3.82 3.85 (s) | 14 | | 2.48–2.68 (m) | | |
| 2 | 4.33/3.71 | 14 | 3.64 | | 2.35–2.75 (m) | |
| 3 | 3.96/3.79 | 13 | 3.78 | | 2.31–2.65 (m) | |
| 4 | 4.31/3.89 3.87 (s) | 14 | | 2.51–2.76 (m) | | |
| 5 | 4.39/3.77 | 14 | 3.61 | | 2.25–2.73 (m) | |
| 6 | 3.93/3.77 | 14 | 3.70 | | 2.31–2.63 (m) | |
| 7 | 4.37/3.81 3.84 (s) | 14 | | 2.48–2.75 (m) | | |
| 8*$^a$ | 4.41/3.94 | 13 | 3.62 | 2.82–3.04 (m) | 2.53 (t) | 7 |
| 9*$^b$ | 4.73–4.96 (m) | | 3.76 | 2.70–2.95 (m) | 2.52 (t) | 7 |
| 10*$^c$ | 4.28/4.08 and 4.27/4.06*$^d$ 4.03/3.84 | 12 13 | | 2.60–2.95 (m) | | |
| 11 | 6.57/4.05 | 14 | 3.72 | 3.68 (s) | 3.07 (s) | |
| 12 | 4.02–4.21 (m) | | 3.86 | 3.64/3.47 J = 14 Hz | 3.19 (s) | |
| 13 | 4.57/3.97 and 4.55/3.95*$^d$ 4.08 (s) | 14 | | 3.61/3.51 and 3.59/3.50 J = 12 Hz 3.68 (s) | | |
| 14 | 4.20 (s) | | 3.66 (s) | | 2.38–2.83 (m) | |
| 15 | 4.09/3.89 | 12 | 3.85 | | 2.43–2.68 (m) | |
| 16 | 4.19 (s) and 3.81–4.05 (m)*$^d$ | | | 2.55–2.86 (m) | | |
| 17 | 4.31/4.09 | 14 | 3.69 | | 2.37–2.84 (m) | |
| 18*$^a$ | 3.90–4.46 (m)*$^d$ | | | 2.56–2.84 (m) | | |

*$^a$measured at 360 MHz
*$^b$measured at 360 MHz in a mixture of deuterochloroform and 6-fold deuterised dimethyl sulfoxide (d$_6$-DMSO)
*$^c$measured at 360 MHz in d$_6$-DMSO
*$^d$mixture of diastereoisomers
s singulet
m multiplet
t triplet

EXAMPLES 19 AND 20

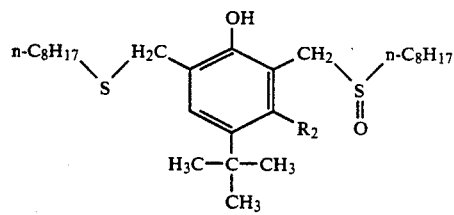

(19)

| Example | Ratio of compound of formula VI/ hydrogen peroxide | Yield |
|---|---|---|
| 19 | 1:1 | 38.5% |
| 20 | 1:2 | 48.8% |

Both compounds are oils.

Characteristic $^1$H-NMR signals of the compounds of Examples 19 and 20, measured in deuterochloroform at 100 MHz (standard: tetramethylsilane), are given in Table 3.

TABLE 3

| Example | Aryl—C$\underline{H_2}$S=O δ [ppm] | $J_{AB}$ [Hz] | Aryl—C$\underline{H_2}$SR δ [ppm] | Aryl—CH$_2$S(=O)C$\underline{H_2}$ δ [ppm] | Aryl—CH$_2$—S—C$\underline{H_2}$ δ [ppm] |
|---|---|---|---|---|---|
| 19 | 4.34/3.87 | 14 | 3.80 | | 2.40–2.74 (m) |
| 20 | 4.33/3.91 and 4.29/3.88 | 13 | | 2.67 (t) J = 7 Hz | | m = multiplet
t = triplet

EXAMPLE 21

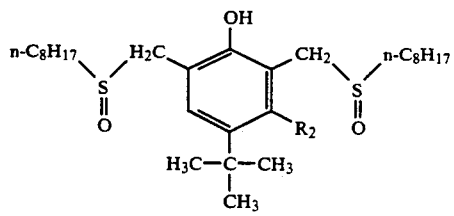

(20)

(21)

4.81 g of m-chloroperbenzoic acid in 200 ml of methylene chloride are added dropwise at room temperature to a solution of 6.0 g of 3,5-bis(n-octylthiomethyl)-2,4,6-

The preparation is as described in Examples 2–18. A 7:3 mixture of hexane/ethyl acetate is used as eluant.

trimethylphenol in 130 ml of methylene chloride. The reaction is heated under reflux for 5 hours and then washed at room temperature with a saturated solution of sodium hydrogencarbonate. The residue of the combined organic phases is filtered over silica gel (eluant: methylene chloride/methanol 40:1). Recrystallisation from methylene chloride/hexane gives 5.1 g of 3,5-bis(n-octylsulfinylmethyl)-2,4,6-trimethylphenol.

Melting point: 175° C.

|  | Elemental analysis |  |  |  |
|---|---|---|---|---|
| calculated: | C | 66.89% | found: C | 66.86% |
|  | H | 9.98% | H | 10.10% |
|  | S | 13.23% | S | 13.24% |

EXAMPLES 22–24

The compounds listed in Table 4 are prepared by the procedure described in Example 21.

TABLE 4

OH
R\  H₃C      CH₃  /R
 \S/              \S/
 O  CH₂    CH₂   O
         CH₃

| Example | R | Melting point [°C.] | Yield [%] |
|---|---|---|---|
| 22 | t-$C_8H_{17}$*1 | 137 | 82.0 |
| 23 | n-$C_{12}H_{25}$ | 165 | 92.0 |
| 24 | $CH_2COO$-2-EH*2 | 92 | 88.0 |

*1 t-$C_8H_{17}$ = 1,1,3,3-tetramethylbutyl
*2 2-EH = 2-ethylhexyl

Characteristic $^1$H-NMR signals of the compounds of Examples 21–24, measured in deuterochloroform at 100 MHz (standard: tetramethylsilane), are given in Table 5.

TABLE 5

| Example | Aryl—C$\underline{H}_2$S=O [ppm] | $J_{AB}$ [Hz] | Aryl—CH₂S(=O)C$\underline{H}_2$ |
|---|---|---|---|
| 21 | 4.28/4.00 | 13 | 2.54–2.95 (m) |
| 22 | 4.08/.,70 and 4.05/3.78* | 13 12.5 | — |
| 23 | 4.30/4.04 | 13 | 2.50–2.95 (m) |
| 24 | 4.48/4.28 | 12.5 | 3.80 (s) |

* mixture of diastereoisomers
m = multiplet
s = singulet

EXAMPLE 25

Stabilisation of polybutadiene rubber (Brabender test)

100 parts of polybutadiene which has been prestabilised with 0.36% of 2,6-di-tert-butyl-p-cresol is kneaded with 0.15% of the stabiliser to be tested in a Brabender plastograph at 160° C. and 60 rpm for 30 minutes.

The machine operates in accordance with the following principle:

Two keader rolls which rotate in a thermostatically heated kneading compartment are driven by a motor which is arranged to oscillate. To overcome the resistance to flow of the plastics material which is present in the kneading compartment, a specific torque is necessary. This torque is registered with the torque pendulum and recorded dependent on the time. The induction time, i.e. the kneading time in minutes until the increase in torque by 100 mp after the minimum torque, is determined from the torque curve. The colour intensity is quantified according to the Yellowness Index (YI) in accordance with ASTM D 1925. Higher values denote more intensive yellowing. The experiments show that the addition of the stabiliser to the plastics material effectively inhibits colour development and keeps the flow resistance constant substantially longer. The results are summarised in Table 6.

TABLE 6

| Stabiliser of Example | Induction time [min] | Yellowness Index |
|---|---|---|
| 1a | 30 | 11 |
| 1b | 30 | 12 |
| 2 | 30 | 13 |
| 5 | 30 | 17 |
| 14 | 30 | 10 |
| 19 | 27 | 13 |
| control* | 9.5 | 31 |

*the control contains no stabiliser of the invention

EXAMPLES 26–35

The stabiliser mixtures listed in Table 7 are prepared by mixing compounds of Example 1a, 1b and/or 1c with 2,4-bis(n-octylthiomethyl)-6-methylphenol in the indicated ratios.

| | Composition in % by weight | | | |
|---|---|---|---|---|
| Example | 1a | 1b | 1c | 2,4-bis(n-octylthiomethyl)-6-methylphenol |
| 26 | 1 | — | — | 99 |
| 27 | — | 1 | — | 99 |
| 28 | — | — | 1 | 99 |
| 29 | 10 | — | — | 90 |
| 30 | 50 | — | — | 50 |
| 31 | — | 50 | — | 50 |
| 32 | — | 90 | — | 10 |
| 33 | 1 | — | 1 | 98 |
| 34 | 10 | 10 | — | 80 |
| 35 | 4 | 1 | 5 | 90 |

EXAMPLE 36

Example 25 is repeated, using in place of 0.15% of the stabilisers tested therein the same amount of the mixtures of Examples 36–35.

These mixtures also prolong the induction time considerably and the Yellowness Index of the polymer is markedly improved.

What is claimed is:

1. A compound of formula I or II or a mixture of compounds I and II

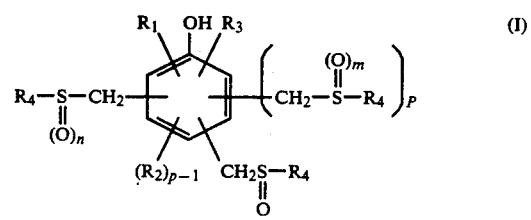
(I)

-continued

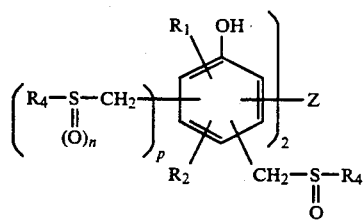

wherein $R_1$ is hydrogen, $C_1$-$C_{18}$alkyl, cyclohexyl or $C_7$-$C_9$-phenylalkyl, $R_2$ and $R_3$ are each independently of the other hydrogen or methyl, $R_4$ is $C_4$-$C_{18}$alkyl, phenyl, $C_7$-$C_9$phenylalkyl, $C_1$-$C_4$alkyl-substituted phenyl, hydroxyethyl or a radical —$(CH_2)_r$COO$R_5$, wherein r is 1 or 2 and $R_5$ is $C_1$-$C_{18}$alkyl, Z is sulfur,

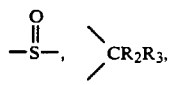

wherein $R_2$ and $R_3$ are as defined above, or are a direct bond, and n, m and p are each independently of one another 0 or 1.

2. A compound according to claim 1, wherein p is 0, $R_4$ is $C_4$-$C_{18}$alkyl, phenyl, $C_7$-$C_9$phenylalkyl, hydroxyethyl or a radical —$CH_2$COO$R_5$, wherein $R_5$ is $C_1$-$C_{18}$alkyl.

3. A compound of formula I according to claim 1.

4. A compound according to claim 3, wherein p is 0, $R_1$ is hydrogen, $C_1$-$C_4$alkyl or cyclohexyl, and $R_4$ is $C_4$-$C_{18}$alkyl, benzyl, phenyl, hydroxyethyl or —$CH_2$COO$R_5$, and $R_5$ is $C_1$-$C_{18}$alkyl.

5. A compound according to claim 4, wherein $R_4$ is $C_8$-$C_{12}$alkyl, benzyl, phenyl, hydroxyethyl or —$CH_2$COO$R_5$.

6. A compound according to claim 3, wherein p is 0 and the groups

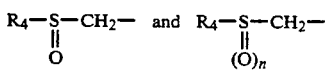

are in 2,4- or 2,6- or 3,5-position to the OH group.

7. A compound according to claim 6, wherein $R_1$ is hydrogen or $C_1$-$C_4$alkyl and $R_4$ is $C_8$-$C_{12}$alkyl, hydroxyethyl or a radical —$CH_2$COO$R_5$, wherein $R_5$ is $C_8$-$C_{12}$alkyl.

8. A compound according to claim 2 of formula III

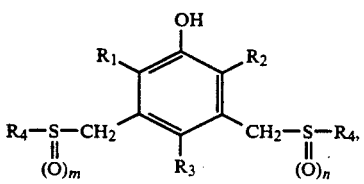

wherein $R_1$ is hydrogen, $C_1$-$C_4$alkyl or cyclohexyl, and $R_2$, $R_3$ and $R_4$ are as defined in claim 2, and n and m are each independently of the other 0 or 1, with the proviso that n+m is $\geq 1$.

9. A compound according to claim 2 of formula IV

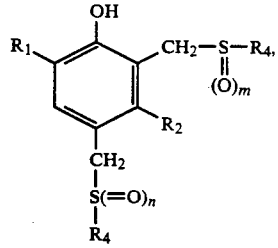

wherein $R_1$ is $C_1$-$C_4$alkyl, $R_2$ and $R_4$ are as defined in claim 2, and n and m are each independently of the other 0 or 1, with the proviso that n+m is $\geq 1$.

10. A compound according to claim 2 of formula V

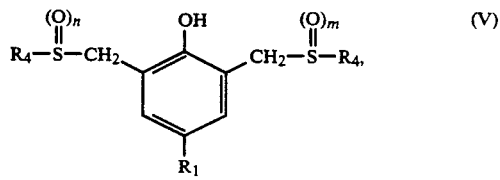

wherein $R_1$ is $C_1$-$C_{12}$alkyl, $R_4$ is as defined in claim 2, and n and m are each independently of the other 0 or 1, with the proviso that n+m is $\geq 1$.

11. A mixture of at least one compound as defined in claim 1 with at least one compound of formula VI or VII

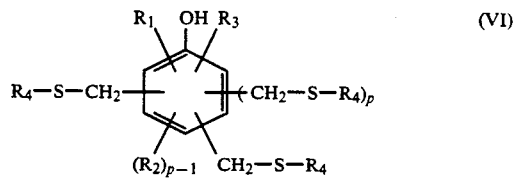

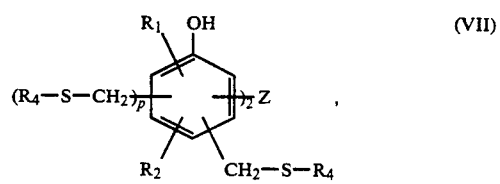

wherein $R_1$, $R_2$, $R_3$, $R_4$, Z and p are as defined in claim 1.

12. A mixture according to claim 11, wherein the components of formulae I and II differ from those of formulae VI and VII only in the feature that the latter contain —S— groups in place of the

groupings but otherwise have the same structure as the former.

13. A mixture according to claim 11, which is obtainable by partial oxidation of at least one compound of formulae VI or VII.

14. A mixture according to claim 11, wherein the ratio of the compounds of formulae I or II to the compounds of formulae VI or VII is 0.5:99.5 to 99.5:0.5.

15. A composition comprising an organic material which is sensitive to oxidative, thermal and/or light-induced degradation and at least one compound of formula I or II according to claim 1 or at least one mixture as defined in claim 11.

16. A composition according to claim 15, comprising at least one compound as defined in claim 2.

17. A composition according to claim 15, wherein the organic material is an organic polymer, a lubricant composition or a hydraulic fluid.

18. A composition according to claim 17, wherein the organic material is a synthetic polymer, a lubricant composition or a hydraulic fluid.

19. A composition according to claim 17, wherein the organic material is an elastomer or a lubricant composition.

20. A composition according to claim 15, comprising at least one compound of formula I or a mixture of compounds of formula I and VI.

21. A process for stabilizing an organic material, which is sensitive to oxidative, thermal and/or light-induced degradation which process comprises incorporating into said material a compound of formula I or II

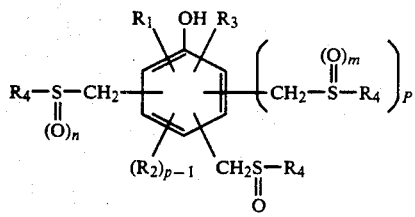
(I)

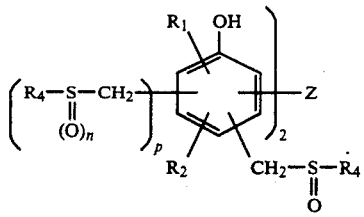
(II)

wherein
R$_1$ is hydrogen, C$_1$-C$_{18}$alkyl, cyclohexyl or C$_7$-C$_9$-phenylalkyl,
R$_2$ and R$_3$ are each independently of the other hydrogen or methyl,
R$_4$ is C$_4$-C$_{18}$alkyl, phenyl, C$_7$-C$_9$phenylalkyl, C$_1$-C$_4$alkyl-substituted phenyl, hydroxyethyl or a radical —(CH$_2$)$_r$COOR$_5$, wherein r is 1 or 2 and R$_5$ is C$_1$-C$_{18}$alkyl, Z is sulfur,

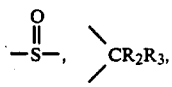

wherein R$_2$ and R$_3$ are as defined above, or are a direct bond, and n, m and p are each independently of one another 0 or 1.

22. A process according to claim 21 wherein the organic material is an organic polymer, a lubricant composition or a hydraulic fluid.

23. A process according to claim 21 wherein the organic material is an elastomer or a lubricant composition.

* * * * *